US010696607B2

(12) United States Patent
Liang et al.

(10) Patent No.: US 10,696,607 B2
(45) Date of Patent: Jun. 30, 2020

(54) LOW INLET TEMPERATURE FOR OXIDATIVE COUPLING OF METHANE

(71) Applicant: SABIC Global Technologies B.V., Bergen op Zoom (NL)

(72) Inventors: Wugeng Liang, Sugar Land, TX (US); Sagar Sarsani, Sugar Land, TX (US); David West, Sugar Land, TX (US); James Lowrey, Sugar Land, TX (US); Aghaddin Mamedov, Sugar Land, TX (US); Istvan Lengyel, Sugar Land, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/579,385

(22) PCT Filed: May 2, 2016

(86) PCT No.: PCT/US2016/030384
§ 371 (c)(1),
(2) Date: Dec. 4, 2017

(87) PCT Pub. No.: WO2016/200504
PCT Pub. Date: Dec. 15, 2016

(65) Prior Publication Data
US 2018/0162785 A1    Jun. 14, 2018

Related U.S. Application Data

(60) Provisional application No. 62/172,406, filed on Jun. 8, 2015.

(51) Int. Cl.
*C07C 2/84*    (2006.01)
*B01J 23/10*    (2006.01)
(Continued)

(52) U.S. Cl.
CPC ............... *C07C 2/84* (2013.01); *B01J 19/245* (2013.01); *B01J 21/08* (2013.01); *B01J 23/10* (2013.01);
(Continued)

(58) Field of Classification Search
CPC ... C07C 2/84; C07C 2521/08; C07C 2523/34; C07C 2523/10; C07C 2523/30;
(Continued)

(56) References Cited

U.S. PATENT DOCUMENTS 5,105,053 A    4/1992    Jacobson et al.
5,405,053 A    4/1995    Zublin
(Continued)

FOREIGN PATENT DOCUMENTS

CN    1045198    9/1999
CN    101664680    3/2010
(Continued)

OTHER PUBLICATIONS

Extended European Search Report issued in European Application No. 16807969.7, dated Sep. 26, 2017.
(Continued)

*Primary Examiner* — Ali Z Fadhel
(74) *Attorney, Agent, or Firm* — Norton Rose Fulbright US LLP

(57) ABSTRACT

Disclosed is a process for producing $C_2+$ hydrocarbons, and systems for implementing the process, that includes providing a reactant feed that includes methane and an oxygen containing gas to a first reaction zone, wherein the temperature of the reactant feed is less than 700° C. contacting the reactant feed with a first catalyst capable of catalyzing an oxidative coupling of methane reaction (OCM) to produce a first product stream that includes C2+ hydrocarbons and heat, and contacting the first product stream with a second
(Continued)

catalyst capable of catalyzing an OCM reaction to produce a second product stream that includes $C_2+$ hydrocarbons, wherein the produced heat is at least partially used to heat the first product stream prior to or during contact with the second catalyst, wherein the amount of $C_2+$ hydrocarbons in the second product stream is greater than the amount of $C_2+$ hydrocarbons in the first product stream.

18 Claims, 7 Drawing Sheets

(51) Int. Cl.
*B01J 23/34* (2006.01)
*B01J 35/00* (2006.01)
*B01J 21/08* (2006.01)
*B01J 37/02* (2006.01)
*B01J 19/24* (2006.01)

(52) U.S. Cl.
CPC .............. *B01J 23/34* (2013.01); *B01J 35/002* (2013.01); *B01J 35/0006* (2013.01); *B01J 37/0236* (2013.01); *B01J 2219/00074* (2013.01); *B01J 2219/24* (2013.01); *C07C 2521/08* (2013.01); *C07C 2523/04* (2013.01); *C07C 2523/10* (2013.01); *C07C 2523/30* (2013.01); *C07C 2523/34* (2013.01); *Y02P 20/52* (2015.11); *Y02P 30/42* (2015.11)

(58) Field of Classification Search
CPC ..... C07C 2523/04; B01J 19/245; B01J 23/34; B01J 23/10; B01J 2219/24; B01J 2219/00074; B01J 35/002; B01J 21/08; B01J 35/0006; B01J 37/0236; Y02P 20/52; Y02P 30/42
See application file for complete search history.

(56) References Cited

U.S. PATENT DOCUMENTS

| | | | |
|---|---|---|---|
| 5,411,927 A | 5/1995 | Choudhary et al. | |
| 2010/0249473 A1 | 9/2010 | Butler | |
| 2010/0331595 A1 | 12/2010 | Chinta et al. | |
| 2012/0041246 A1* | 2/2012 | Scher .................... | B01J 21/066 585/500 |
| 2013/0023709 A1 | 1/2013 | Cizeron et al. | |
| 2013/0225884 A1 | 8/2013 | Weinberger et al. | |
| 2014/0107385 A1* | 4/2014 | Schammel ............. | B01J 8/0496 585/501 |
| 2014/0171707 A1* | 6/2014 | Nyce ........................ | C07C 2/04 585/329 |
| 2014/0274671 A1 | 9/2014 | Schammel et al. | |
| 2015/0321974 A1* | 11/2015 | Schammel ............. | B01J 8/0496 585/501 |

FOREIGN PATENT DOCUMENTS

| | | |
|---|---|---|
| EP | 0582004 | 1/1997 |
| WO | WO 2013/177433 | 11/2013 |

OTHER PUBLICATIONS

Ferreira et al., "Ce-doped $La_2O_3$ based catalyst for the oxidative coupling of methane," *Catalysis Communication*, 42:50-53, (2013).
Hu et al., "Dual catalyst bed for the oxidation of $CH_4$ simultaneously to $C_2H_4$ and syngas," *AIChE Journal*, 53(11):2925-2931, (2007).
International Preliminary Report on Patentability issued in International Application No. PCT/US2016/030384, dated Jun. 20, 2017.
International Search Report and Written Opinion issued in International Application No. PCT/US2016/030384, dated Nov. 8, 2016.
Mahmoodi et al., "Effect of Additives on $Mn/SiO_2$ Based Catalysts on Oxidative Coupling of Methane," *Iranian Journal of Chemistry and Chemical Engineering*, 30(1):29-36, (2011).
Makhlin et al., "Oxidative dimerization of methane: Kinetics, mathematical modeling, and optimization with La/Ce catalysts" *Russian Journal of General Chemistry*, 79(9):2016-2023, (2009).
Noon et al., "Oxidative coupling of methane with $La_2O_3$—$CeO_2$ nanofiber fabrics: A reaction engineering study," *Journal of Natural Gas Science and Engineering*, 18:406-411, (2014).
Sadjadi et al., "Feasibility study of the Mn—$Na_2WO_4/SiO_2$ catalytic system for the oxidative coupling of methane in fluidized-bed reactor" *Catalysis Science & Technology, E-Pub*, 5(2):942-953, (2014).
Salerno, "Optimal Synthesis of Downstream Processes using the Oxidative Coupling of Methane Reaction," Technical University of Berlin, PhD Thesis, (2013).
Taylor et al., "Lanthanum catalysts, for $CH_4$ oxidative coupling: A comparison of the reactivity of phases," *Industrial and Engineering Chemistry Research*, 30(5):1016-1023, (1991).
Zhang et al., "Oxidative coupling of methane using microwave dielectric heating," *Applied Catalysis A: General*, 249(1):151-164, (2003).

* cited by examiner

LOW INLET TEMPERATURE FOR OXIDATIVE COUPLING OF METHANE

CROSS REFERENCE TO RELATED APPLICATIONS

This application is a national phase application under 35 U.S.C. § 371 of International Application No. PCT/US2016/030384 filed May 2, 2016, which claims the benefit of priority of U.S. Provisional Patent Application No. 62/172,406, filed Jun. 8, 2015. The entire contents of each of the above-referenced disclosures are specifically incorporated herein by reference without disclaimer.

BACKGROUND OF THE INVENTION

A. Field of the Invention

The invention generally concerns systems and methods for the production of $C_{2+}$ hydrocarbons from methane ($CH_4$) and oxygen ($O_2$). In particular, the systems and methods allow a reactant feed having a relatively low temperature to be used.

B. Description of Related Art

Due to advancements in technology, more and more shale reservoirs are being produced, which in turn gives rise to more and more natural gas being produced. Natural gas is a naturally occurring mixture of hydrocarbon gases. Natural gas includes methane and contains up to about twenty percent concentration of higher hydrocarbons such as ethane and small quantities of impurities such as carbon dioxide and hydrogen sulfide. While natural gas is an abundant hydrocarbon resource it has a low economic value as compared to more valued hydrocarbons having a carbon number of 2 or greater (e.g., ethylene, ethane, propane, etc.), which can be used to produce a wide range of products. For example, ethylene is a key raw material of the petrochemical industry for making polyethylene, ethylene oxide and other petrochemical products. Many of these products are used as to produce a wide range of products such as break-resistant containers and packaging materials. For industrial scale applications, ethylene is currently produced by steam or catalytic cracking of products obtained from distillation gaseous or light hydrocarbons, which include ethane and higher hydrocarbons. The resulting product is subjected to separation processes to remove ethylene.

Methane can be used to produce ethane and/or ethylene by oxidative coupling of the methane with itself. Extensive research and development has been devoted to the technology of oxidative coupling, however, no process has been successfully commercialized. One of the key challenging issues is the high reaction temperature required to make the reaction proceed. The high temperatures are required because the dissociation strength (bond dissociation enthalpies) of the tetrahedral C—H bonds in methane is 435 kilojoules per mole (kJ/mol), which makes it less reactive, and difficult to undergo oxidative conversion to form ethylene. The oxidative coupling of the methane is represented by the following equations:

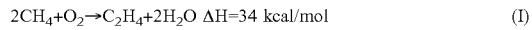

$$2CH_4 + O_2 \rightarrow C_2H_4 + 2H_2O \quad \Delta H = 34 \text{ kcal/mol} \quad (I)$$

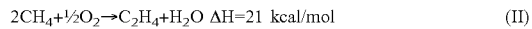

$$2CH_4 + \tfrac{1}{2}O_2 \rightarrow C_2H_4 + H_2O \quad \Delta H = 21 \text{ kcal/mol} \quad (II)$$

As shown in Equations (I) and (II), oxidative conversion of methane to ethylene is exothermic. Excess heat produced from these reactions can push conversion of methane to carbon monoxide and carbon dioxide rather than the desired $C_2$ hydrocarbon product:

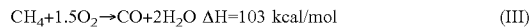

$$CH_4 + 1.5O_2 \rightarrow CO + 2H_2O \quad \Delta H = 103 \text{ kcal/mol} \quad (III)$$

$$CH_4 + 2O_2 \rightarrow CO_2 + 2H_2O \quad \Delta H = 174 \text{ kcal/mol} \quad (IV)$$

The excess heat from the reactions in Equations (III) and (IV) further exasperate this situation, thereby substantially reducing the selectivity of ethylene production when compared with carbon monoxide and carbon dioxide production.

Many attempts to lower the ignition and reaction temperatures have involved the use of catalysts, however, temperatures of higher than 750° C. are still necessary to achieve satisfactory results. In conventional methods, the reactant feed is heated to the reaction temperature (e.g., greater than 750° C.) in a furnace (e.g., a natural gas furnace) before entering the reactor. In order to heat the mixture to the required temperature, the furnace temperature has to be higher than the required temperature. Thus, a high temperature furnace is needed and a substantial amount of energy (e.g., electricity derived from hydrocarbons) or fuel is required to generate the heat (See, for example, Salerno, Ph.D. Thesis, Technical University of Berlin, page 42, FIG. 2.4). Furthermore, operation at such high temperature requires special materials for reactor construction. Additionally, at high temperatures agglomeration (coking) of methane oxidative coupling catalysts can take place. Such agglomeration can cause deactivation of the catalyst.

There have been many attempts to provide improved catalysts to promote the oxidative coupling of methane. U.S. Patent Application Publication No. 2014/0107385 to Schammel et al.; et al. describes systems of a series of catalyst beds where the inlet temperature is less than 600° C. Further, all of the catalytic beds are kept at the same temperature throughout the reaction process by removing thermal energy generated during the upstream reactions, which results in an inefficient use of energy during its process.

SUMMARY OF THE INVENTION

The present application provides a solution to the problems associated with elevated feed temperatures, elevated ignition temperatures, and reaction temperatures required in the production of $C_2+$ hydrocarbons by oxidative coupling of methane (OCM). In one particular non-limiting embodiment, the solution resides in the combination two catalysts having different catalytic activities, $C_2+$ hydrocarbon selectivities and the placement of the catalysts during the reaction. The first catalyst, which can be placed upstream from the second catalyst, can initiate the oxidative coupling reaction at lower temperatures (e.g., 700° C. or less) compared to downstream oxidative coupling catalysts. Thus, the reactant mixture does not need to be heated to temperatures used in conventional process, which results in a more energy efficient process (e.g., less fuel needs to be burned to heat a furnace positioned prior to the reactor). Heat generated between the reactant feed and the first catalyst can be used to heat the first product stream. The second catalyst, which can be positioned downstream from the first catalyst, can then be used to further process the product stream produced by the upstream catalyst into the desired $C_2+$ hydrocarbons. Such a combination produces a greater amount of $C_2+$ hydrocarbons in the second product stream than those produced in the first product stream. Without wishing to be bound by theory, it is believed that this combination and placement of the catalysts allows for (1) the reactant feed to enter the reactor at a lower average temperature relative to average temperatures conventionally used for oxidative coupling of methane and (2) increase the overall selectivity of $C_2+$ hydrocarbon production by efficiently managing the temperature and, thus, maximizing the energy generated of the overall reaction process. The present invention, therefore, provides a commercially viable OCM process.

In one aspect of the present invention there is disclosed a method of producing $C_2+$ hydrocarbons from an oxidative coupling of methane reaction. The method can include (a) providing a reactant feed that includes methane and an oxygen containing gas to a first reaction zone, wherein the temperature of the reactant feed is less than 700° C., 275° C. to less than 700° C., preferably 300° C. to 550° C., or more preferably 300° C. to 450° C.; (b) contacting the reactant feed with a first catalyst capable of catalyzing an oxidative coupling of methane reaction to produce a first product stream that includes $C_2+$ hydrocarbons and heat; and (c) contacting the first product stream with a second catalyst capable of catalyzing an oxidative coupling of methane reaction to produce a second product stream that includes $C_2+$ hydrocarbons, wherein heat produced in step (b) is at least partially used to heat the first product stream prior to or during contact with the second catalyst, and wherein the amount of $C_2+$ hydrocarbons in the second product stream is greater than the amount of $C_2+$ hydrocarbons in the first product stream. In a particular instance, the oxidative coupling of methane reaction in step (b) can occur/take place at a temperature of less than 700° C., preferably 275° C. to less than 700° C., most preferably 300° C. to 550° C., or more preferably 300° C. to 450° C., and the oxidative coupling of methane reaction in step (c) can occur at a temperature of at least 700° C., preferably 700° C. to 1000° C., or more preferably 700° C. to 900° C. Still further, the temperature of the methane reaction in step (b) can be less than or equal to 700° C., 300° C. to less than 700° C., 400° C. to 550° C., or 425° C. to 525° C. The temperature of the first product stream just prior to or during contact with the second catalyst can be at least 700° C., preferably 700° C. to 1000° C., or more preferably 700° C. to 900° C. The reaction can be operated under atmosphere pressure and it can also be operated under elevated pressure. The methane to oxygen ($CH_4/O_2$) ratio can be less than 10, preferably less than 7 and more preferably less than 4. The gas hourly space velocity (GHSV) can be 500 $hr^{-1}$, 1000 $hr^{-1}$ or more, more 10,000 $hr^{-1}$ or more, or 50,000 $hr^{-1}$ or more. The first and second catalysts that can be used include any one of the catalysts described throughout the specification. The first product stream can be optionally mixed with additional oxygen containing gas and the contacted with a second catalyst positioned downstream of the first catalyst. The first and/or second catalyst can be any supported, non-supported, or bulk metal catalyst suitable for oxidative coupling of methane. The first and second catalysts can be positioned in a first and second catalytic bed located in sequence, where the second bed is downstream from the first bed. The first catalyst can have a $C_2+$ hydrocarbon selectivity of at least 60%, 60% to 80%, or 60% to 70% and an oxygen conversion of at least 90%. A non-limiting example of a first catalyst is a lanthanum-cerium oxide catalyst that includes a $La(OH)_3$ crystal phase. The second catalyst can have a higher selectivity of $C_2+$ hydrocarbons than the first catalyst (e.g. $C_2+$ hydrocarbon selectivity is at least 70%, 70% to 90%, or 75% to 80% and an oxygen conversion of at least 90%). A non-limiting example of a second catalyst is $Mn-Na_2WO_4$ on $SiO_2$.

In another aspect of the present invention there is disclosed a system for producing $C_2+$ hydrocarbons. The system can include an inlet for a reactant feed, a first reaction zone that is configured to be in fluid communication with the inlet, a second reaction zone that is configured to be in fluid communication with the first reaction zone and configured to receive a first product stream from the first reaction zone, and an outlet configured to be in fluid communication with second reaction zone and configured to remove a second product stream that includes $C_2+$ hydrocarbons from the reaction zone. The reactant stream can include methane and an oxygen containing gas. The first and second catalysts are capable of catalyzing an oxidative coupling of methane reaction. The first catalyst is positioned near or at the inlet of the reactor and is contacted with the reactant feed prior to contact of the feed with the second catalyst. The temperature of the reactant feed entering the inlet can be 700° C. or less, preferably 275° C. to less than 700° C., preferably 300° C. to 550° C., or more preferably 300° C. to 450° C. At such low temperatures, the first catalyst is capable of igniting the reactant feed and maintaining the reaction. Heat generated by the first catalyst can be transferred to the first product stream and/or to the second catalyst. Reaction conditions can include an average temperature of less than 1000° C., preferably 275° C. to less than 700° C., more preferably 400° C. to 550° C., and most preferably 400° C. to 525° C. The methane to oxygen ($CH_4/O_2$) ratio can be less than 10, preferably less than 7 and more preferably less than 4. The gas hourly space velocity (GHSV) 500 $hr^{-1}$ or more, 1000 $hr^{-1}$ or more, more 10,000 $hr^{-1}$ or more, or 50,000 $hr^{-1}$ or more. The reaction can be operated under atmosphere pressure and it can also be operated under elevated pressure. In some embodiments, the reactant feed is heated to a temperature less than 700° C., preferably 275° C. to less than 700° C., more preferably 300° C. to 550° C., and most preferably 300° C. to 450° C. The product stream generated using the first catalyst can be mixed with additional oxygen supplied through a second inlet and contacted with the second catalyst. The first product stream can be heated to average temperature of at least 700° C., or 700° C. to 1000° C., 700° C. to 900 prior to or during contact of the first product steam with the second catalyst. Reaction conditions for contacting the first product stream with the second catalyst can include an average temperature of at least 600° C., or 700° C. to 1000° C., 700° C. to 900. Over the second catalyst, the methane to oxygen ($CH_4/O_2$) ratio can be less than 10, preferably less than 7 and more preferably less than 4. The gas hourly space velocity (GHSV) can be higher or the same as the GHSV used in the first reaction zone, (e.g., 500 $hr^{-1}$ or more, 1000 $hr^{-1}$ or more, 10,000 $hr^{-1}$ or more, or 50,000 $hr^{-1}$ or more, or 80,000 $hr^{-1}$ or more, preferably higher than 50,000 $hr^{-1}$). The amount of $C_2+$ hydrocarbons in the second product stream can be greater than the amount of $C_2+$ hydrocarbons in the first product stream. In some aspects of the invention, the second catalyst or additional catalyst (e.g., 3, 4, 5, etc.) can be positioned downstream of the first catalyst. The first second and/or additional catalysts can be any supported, non-supported, or bulk metal catalyst described throughout the specification and/or suitable for oxidative coupling of methane. The first catalyst has a $C_2+$ hydrocarbon selectivity of at least 60%, 60% to 80%, or 60% to 70% and an oxygen conversion of at least 90%. A non-limiting example of a first catalyst is a lanthanum-cerium oxide catalyst that includes a $La(OH)_3$ crystal phase. The second catalyst can have a higher $C_2+$ hydrocarbons selectivity than the first catalyst (e.g., a $C_2+$ hydrocarbon selectivity of at least 70%, 70% to 90%, or 75% to 80%) and an oxygen conversion of at least 90%). A non-limiting example of a second catalyst is Mn—$Na_2WO_4$ on $SiO_2$.

The resulting the $C_2$+ hydrocarbons and water produced from the methods and systems of the present invention can be collected in a collection device and/or transported via piping to separation unit. In the separation unit, the $C_2$+ hydrocarbons are separated using known separation techniques, for example, distillation, absorption, membrane technology to produce an ethylene product.

In another aspect of the invention, a metal oxide catalyst capable of catalyzing an oxidative coupling of methane reaction is described. The metal oxide catalyst includes a lanthanum (La) cerium (Ce) metal oxide and a lanthanum hydroxide ($La(OH)_3$) crystalline phase, and the metal oxide catalyst is capable of catalyzing the production of $C_2$+ hydrocarbons from methane and oxygen. The molar ratio of La to Ce in the catalyst can be from 1<La:Ce≤30 (e.g., 5<La:Ce≤30, and 5<La:Ce≤15). The catalyst is in crystalline form and the La and Ce are incorporated into the crystal lattice structure. At La to Ce molar ratios of greater than 1, the $La(OH)_3$ crystalline phase is also present in the crystal lattice of the catalyst. In some aspects of the invention, the metal oxide catalyst is a bulk metal catalyst. The metal oxide catalyst is capable of catalyzing the production of $C_2$+ hydrocarbons from methane and oxygen at a temperature of less than 1000° C., preferably 300° C. to less than 700° C., more preferably 400° C. to 550° C., and most preferably 400° C. to 525° C. Under reaction conditions including a temperature of 450° C. to 500° C. at a methane/oxygen ratio equal to 7.4 ($CH_4/O_2$=7.4), the metal oxide catalyst can have a $C_2$+ hydrocarbon selectivity of at least 60%, 60% to 80%, or 60% to 70% and an oxygen ($O_2$) conversion of at least 90%. When the metal oxide catalyst is contacted with a reactant feed that includes methane and an oxygen containing gas (e.g., air, oxygen, oxygen enriched air, or combinations thereof) at a desired temperature (e.g., an average temperature of less than 1000° C., preferably 300° C. to less than 700° C., more preferably 400° C. to 550° C., and most preferably 400° C. to 525° C.) at least a portion of the methane in the reactant feed can be formed into $C_2$+ hydrocarbons.

In another aspect of the invention a method of making the metal oxide catalyst of the present invention is described. The method can include obtaining a solution mixture that includes lanthanum and cerium salts such as lanthanum and cerium nitrate, having molar ratio of La to Ce of 1<La:Ce≤30, removing the solvent at a temperature of about 120 to 130° C. to obtain a dried mixture, and calcining the dried mixture at an average temperature of 400° C. to 850° C., preferably 500° C. to 700° C., most preferably 600 to 650° C., for a sufficient period of time (e.g., for 3 and 12 hours, preferably 4 and 8 hours) to obtain the metal oxide catalyst described above and throughout the specification.

In the context of the present invention, embodiments 1 to 34 are described. Embodiment 1 is a method of producing $C_2$+ hydrocarbons from an oxidative coupling of methane reaction. The method includes (a) providing a reactant feed that includes methane and an oxygen containing gas to a first reaction zone, wherein the temperature of the reactant feed is less than 700° C., 275° C. to less than 700° C., preferably 300° C. to 550° C., or more preferably 300° C. to 450° C.; (b) contacting the reactant feed with a first catalyst capable of catalyzing an oxidative coupling of methane reaction to produce a first product stream that includes C2+ hydrocarbons and heat; and (c) contacting the first product stream with a second catalyst capable of catalyzing an oxidative coupling of methane reaction to produce a second product stream that includes $C_2$+ hydrocarbons, wherein heat produced in step (b) is at least partially used to heat the first product stream prior to or during contact with the second catalyst, and wherein the amount of $C_2$+ hydrocarbons in the second product stream is greater than the amount of $C_2$+ hydrocarbons in the first product stream. Embodiment 2 is the method of embodiment 1, wherein the oxidative coupling of methane reaction in step (b) occurs at a temperature of less than 700° C., 275° C. to less than 700° C., preferably 300° C. to 550° C., or more preferably 300° C. to 450° C.; and the oxidative coupling of methane reaction in step (c) occurs at a temperature of at least 700° C., preferably 700° C. to 1000° C., or more preferably 700° C. to 900° C. Embodiment 3 is the method of embodiment 2, wherein the temperature of the reactant feed just prior to or during contact with the first catalyst is 300° C. to 550° C., or more preferably 300° C. to 450° C., and the temperature of the first product stream just prior to or during contact with the second catalyst is at least 700° C., preferably 700° C. to 1000° C., or more preferably 700° C. to 900° C. Embodiment 4 is the method of any one of embodiments 1 to 3, wherein the first catalyst and/or second catalyst are each individually a bulk metal catalyst or a supported catalyst. Embodiment 5 is the method of embodiment 4, wherein the first catalyst, the second catalyst or both includes manganese or a compound thereof, tungsten or a compound thereof, lanthanum or a compound thereof, sodium or a compound thereof, cerium or a compound thereof, silicon or a compound thereof, and any combination thereof. Embodiment 6 is the method of embodiment 5, wherein the first catalyst includes a lanthanum (La) cerium (Ce) metal oxide having a lanthanum hydroxide ($La(OH)_3$) crystalline phase. Embodiment 7 is the method of embodiment 6, wherein the first catalyst is a bulk metal oxide catalyst. Embodiment 8 is the method of embodiment 4, wherein the second catalyst is a supported catalyst and wherein the support is silicon dioxide, lanthanum oxide, or aluminum oxide, or a combination thereof. Embodiment 9 is the method of embodiment 8, wherein the second catalyst that includes Mn—$Na_2WO_4$/$SiO_2$ and the first catalyst includes a lanthanum (La) cerium (Ce) metal oxide having a lanthanum hydroxide ($La(OH)_3$) crystalline phase. Embodiment 10 is the method of any one of embodiments 1 to 9 wherein the first product stream, prior to being contacted with the second catalyst, is contacted with an oxygen gas feed. Embodiment 11 is the method of embodiment 10, wherein the second product stream is contacted with an oxygen gas feed. Embodiment 12 is the method of any one of embodiments 1 to 10, wherein the first catalyst is positioned in a first catalytic bed and the second catalyst is in a second catalytic bed. Embodiment 13 is the method of any one of embodiments 1 to 12, wherein $C_2$+ hydrocarbon selectivity in the first reaction zone is at least 60%, or 60% to 80%, or 60% to 70%. Embodiment 14 is the method of embodiment 13, wherein overall $C_{2+}$ hydrocarbon selectivity of the second catalyst is at least 70%, preferably 70% to 95%, and most preferably 75% to 90%. Embodiment 15 is the method of embodiment 14, wherein the overall $O_2$ conversion is at least 95% or is 100%.

Embodiment 16 is a system for producing $C_2$+ hydrocarbons. The system includes (a) an inlet for a reactant feed that includes methane and an oxygen containing gas, wherein the temperature of the reactant feed entering the inlet is 700° C. or less, preferably 275° C. to less than 700° C., more preferably 300° C. to 550° C., and most preferably 300° C. to 450° C.; (b) a first reaction zone that is configured to be in fluid communication with the inlet, wherein the first reaction zone includes a first catalyst capable of catalyzing an oxidative coupling of methane reaction and producing a first product stream; (c) a second reaction zone that is configured to be in fluid communication with the first reaction zone and receive the first product stream from the first reaction zone, wherein the second reaction zone includes a second catalyst capable of catalyzing an oxidative coupling of methane reaction; and (d) an outlet configured to be in fluid communication with the second reaction zone and configured to remove a second product stream that includes $C_2+$ hydrocarbons from the reaction zone, wherein the amount of $C_2+$ hydrocarbons in the second product stream is greater than the amount of $C_2+$ hydrocarbons in the first product stream. Embodiment 17 is the system of embodiment 16, wherein the temperature of the second reaction zone is greater than the temperature of the first reaction zone. Embodiment 18 is the system of embodiment 17, wherein at least a portion of the heat from the first reaction zone is used to heat the second reaction zone or is used to heat the first product stream or is used to heat both. Embodiment 19 is the system of embodiment 18, wherein the first product stream is included in in the second reaction zone and has a temperature of at least 750° C., preferably 750° C. to 1000° C., or more preferably 700° C. to 900° C. Embodiment 20 is the system of embodiment 19, wherein the first catalyst is a bulk metal catalyst or a supported catalyst. Embodiment 21 is the system of embodiment 20, wherein the first catalyst includes manganese or a compound thereof, tungsten or a compound thereof, lanthanum or a compound thereof, sodium or a compound thereof, cerium or a compound thereof, silicon or a compound thereof, and any combination thereof. Embodiment 22 is the system of embodiment 21, wherein the first catalyst includes a lanthanum (La) cerium (Ce) metal oxide having a lanthanum hydroxide $(La(OH)_3)$ crystalline phase. Embodiment 23 is the system of embodiment 22, wherein the first catalyst is a bulk metal catalyst. Embodiment 23 is the system of embodiment 20, wherein the first catalyst is a supported catalyst and wherein the support is silicon dioxide, lanthanum oxide, or aluminum oxide, or a combination thereof. Embodiment 24 is the system of any one of embodiments 20 to 24, wherein the second catalyst is a bulk metal catalyst or a supported catalyst. Embodiment 25 is the system of embodiment 25, wherein the second catalyst is a supported catalyst and wherein the support is silicon dioxide, lanthanum oxide, or aluminum oxide, or a combination thereof. Embodiment 26 is the system of embodiment 26, wherein the second catalyst is a supported catalyst that includes $Mn-Na_2WO_4/SiO_2$. Embodiment 27 is the system of embodiment 27, wherein the second catalyst is a bulk metal catalyst that includes manganese or a compound thereof, tungsten or a compound thereof, lanthanum or a compound thereof, sodium or a compound thereof, cerium or a compound thereof, silicon or a compound thereof, and any combination thereof. Embodiment 28 is the system of any one of embodiments 16 to 28, wherein the second reaction zone further including the second product stream. Embodiment 30 is the system of embodiment 29, further including at least one collection device that is capable of collecting the second product stream. Embodiment 31 is the system of any one of embodiments 16 to 30, further including an outlet positioned downstream from the first reaction zone and is configured to remove at least a portion of the first product stream from the reaction zone. Embodiment 32 is the system of any one of embodiments 16 to 31, wherein the system further including a second inlet that is positioned upstream from the outlet and is configured to introduce an oxygen containing gas feed to the (i) first product stream prior to contacting the second catalyst or (ii) second product stream. Embodiment 33 is the system of any one of embodiments 16 to 32, wherein the system further including a third inlet configured to introduce oxygen containing gas feed to the reactant to the reactant feed prior to contacting the first catalyst. Embodiment 34 is the system of any one of embodiments 16 to 33, wherein the reaction zone is a continuous flow reactor. Embodiment 35 is the system of embodiment 34, wherein the continuous flow reactor is a fixed-bed reactor, a fluidized reactor, or a moving bed reactor.

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "bulk metal oxide catalyst" as that term is used in the specification and/or claims, means that the catalyst includes at least one metal, and does not require a carrier or a support.

The terms "$C_x+$ hydrocarbons" where x is an integer refers to a mixture of hydrocarbons having a carbon number of x and more. For example $C_2+$ hydrocarbons is a mixture of hydrocarbons having 2 and more carbon numbers.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The terms "wt. %" or "vol. %" refers to a weight or volume percentage of a component, respectively, based on the total weight or the total volume of material that includes the component. In a non-limiting example, 10 grams of metal in 100 grams of the catalyst is 10 wt. % of metal.

The use of the words "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The systems and methods of the present invention can "comprise," "consist essentially of," or "consist of" particular ingredients, components, compositions, etc. disclosed throughout the specification. With respect to the transitional phase "consisting essentially of," in one non-limiting aspect, a basic and novel characteristic of the catalysts of the present invention are their abilities to catalyze oxidative coupling of methane at lower temperatures (e.g., 700° C. or less).

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

Figure 1:
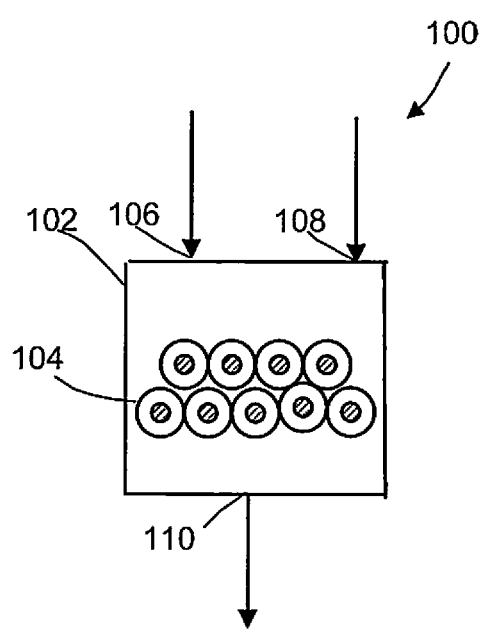
FIG. 1 is a schematic of an embodiment of a system to produce ethylene using the catalytic material of the present invention.

While the invention is susceptible to various modifications and alternative forms, specific embodiments thereof are shown by way of example in the drawings and may herein be described in detail. The drawings may not be to scale.

DETAILED DESCRIPTION OF THE INVENTION

The present application provides for an economically viable OCM process that utilizes a relatively low inlet temperature (e.g., 700° C. or less) for a reactant feed having $CH_4$ and $O_2$. At least two catalysts positioned upstream/downstream with respect to one another are used in the process. The temperature of the reactant feed upon contacting the upstream catalyst can be 700° C. or less. In addition to the amounts of $C_2+$ hydrocarbon products produced, heat is produced due to the exothermic OCM reaction. The produced heat can then be used to heat the initial product stream prior to or during contact with the downstream catalyst. Therefore, and without wishing to be bound by theory, the present invention leverages the exothermic OCM process as a heat source to reach the typical OCM reaction temperature (e.g., greater than 750° C.). In particular, the heat generated by the reactant feed coming into contact with the upstream catalyst (upstream OCM reaction) can then be used to heat the initial product stream prior to or during contact with the downstream catalyst (downstream OCM reaction). This allows for an increase in $C_2+$ hydrocarbon selectivity with the downstream OCM reaction relative to the upstream OCM reaction. As illustrated in a non-limiting manner in the Examples, this allows for energy savings by using a relatively low inlet temperature (e.g., 700° C. or less) while still producing a sufficient amount of $C_2+$ hydrocarbon products. The end result is an economically viable OCM process.

These and other non-limiting aspects of the present invention are discussed in further detail in the following sections.

A. Catalytic Material

1. First/Upstream Catalytic Material

The metals that can be used in the context of the present invention to create bulk metal oxides or supported catalysts include at least two metals ($M^1$ and $M^2$) from the lanthanide series (Group IIIB, Column 3) of the Periodic Table. The metals or metal compounds can be purchased from any chemical supplier such as Sigma-Aldrich, Alfa-Aeaser, Strem, etc. Lanthanides metals and metal compounds include lanthanum, cerium, praseodymium (Pr), neodymium (Nd), promethium (Pm), terbium (Tb), dysprosium (Dy), holmium (Ho), erbium (Er), thulium (Tm), lutetium (Lu) or any combination thereof, with lantheum and cerium oxides being preferred. In a particular embodiment, the catalyst does not contain a dopant. In a preferred embodiment, the catalyst consists essentially of lanthanum-cerium oxide and lanthanum hydroxide. In a non-limiting example, lanthanum nitrate and cerium nitrate are used in combination to create the catalysts of the present invention.

The catalysts are crystalline in structure and can include one or more crystalline phases. The phases can have a common crystal framework and structure. At least one phase contains a trinary structure of two metals and oxygen ($M^1M^2O$) where at least one of $M^1$ and $M^2$ is in a trivalent state. For example, the metal oxide catalyst can be La—Ce oxides, where La is in the trivalent state (III).

A second phase is a $M^1(OH)_3$ crystal phase, where $M^1$ is the trivalent ion of the $M^1M^2O$ compound, (e.g., lanthanum). In the most preferred embodiment, $M^1$ is lanthanum and the second phase is $La(OH)_3$. The $M^1(OH)_3$ crystal phase is believed to have a hexagonal crystal structure and that the $M^1(OH)_3$ (e.g., $La(OH)_3$) is incorporated in the $M^1M^2O$ (e.g., La—Ce oxide) crystal lattice.

The bulk metal oxide catalysts of the present invention can be made by processes that provide a crystalline structure as exemplified in the Examples section. A non-limiting example includes dissolving salts of lantheum and cerium (for example, $La(NO_3)_3$ and $Ce(NO_3)_3$) in de-ionized water with agitation. The metal salts can be in a 2:1 to 30:1 molar ratio, preferably a 5:1 to 30:1, or most preferably a 5:1 to 15:1 molar ratio, of $M^1:M^2$ (for example, $La(NO_3)_3$ and $Ce(NO_3)_3$). The molar ratio of $M^1$ to $M^2$ (e.g., La:Ce) can be greater than 1, or 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30 or any value there between. In a particular instance, the $M^1$ to $M^2$ (e.g., La:Ce) molar ratio is from 5 to 30, 5 to 15, or 7 to 12. The aqueous mixture of the salts can be dried at a temperature from 110° C. to 130° C., for example, 125° C. The dried material can be calcined by heating the pellets to an average temperature between 400° C. and 850° C., 500° C. to 700° C., with 600° C. and 650° C. being preferred, at a rate of about 1° C. per minute and holding at between 600° C. and 650° C. for 3 to 12 hours, or 4 to 8 hours, and then cooled at a rate of about 1° C. per minute to ambient temperature (about 72 to 80° C.). In a preferred aspect of the invention, the calcining temperature is 650° C. at 4 to 8 hours. The resulting catalyst has discrete $M^1(OH)_3$ (e.g., $La(OH)_3$) phase in the crystal lattice). In a preferred embodiment, the La—Ce oxide has $La(OH)_3$ incorporated in its crystal lattice.

The bulk metal oxide catalysts of the present invention can be put on a support. Supported metal oxide catalysts of the present invention can be made by generally known catalyst preparation techniques. The support can be $Al_2O_3$, $SiO_2$ or other materials. In some embodiments, the support may be combined with the catalytic metal to form a catalyst (for example, an incipient impregnation technique). In a particular embodiment, the catalyst is not a nanowire or present in a nanowire substrate.

As illustrated in the Examples section, the produced bulk metal oxide catalysts of the invention are coke resistant materials at elevated temperatures, such as those typically used in oxidative coupling of methane reactions (e.g., 400° C. up to 1000° C. or range from 400° C., 450° C., 500° C., 525° C., 550° C., 600° C., 700° C., 750° C., to 950° C.). Further, the produced catalysts can be used effectively in oxidative coupling reactions of methane at an average temperature range from 275° C. up to 1000° C. or from 400° C. to 525° C., at a gas hourly space velocity (GHSV) range from 500 to 100,000 h$^{-1}$ or more at atmospheric or elevated pressures, preferably a temperature of 400° C. to 525° C. and a GHSV of 50,000 h$^{-1}$ or more. The metal oxide catalyst can have a $C_2$+ hydrocarbon selectivity of at least 60%, 60% to 80%, or 60% to 70%, or at least 60%, 65%, 70%, 75%, 80% or any range there between. The metal oxide catalyst can have $O_2$ conversion of at least 90% or 100%.

2. Additional Catalytic Material

Additional catalysts can be used in combination with the catalyst of the present invention. The additional catalysts (e.g., a second catalyst, third catalyst, fourth catalyst, etc.) can be positioned downstream of the catalyst (first catalyst). The second catalyst can be the same catalysts, different catalysts, or a mixture of catalysts. The catalysts can be supported, bulk metal catalysts, or unsupported catalysts. The support can be active or inactive. The catalyst support can include MgO, $Al_2O_3$, $SiO_2$, or the like. All of the support materials can be purchased or be made by processes known to those of ordinary skill in the art (e.g., precipitation/co-precipitation, sol-gel, templates/surface derivatized metal oxides synthesis, solid-state synthesis, of mixed metal oxides, microemulsion technique, solvothermal, sonochemical, combustion synthesis, etc.). One or more of the catalysts can include one or more metals or metal compounds thereof. Catalytic metals include Li, Na, Ca, Cs, Mg, La, Ce, W, Mn, Ru, Rh, Ni, and Pt. Non-limiting examples of catalysts of the invention include La on a MgO support, Na, Mn, and $La_2O_3$ on an aluminum support, Na and Mn oxides on a silicon dioxide support, $Na_2WO_4$ and Mn on a silicon dioxide support, or any combination thereof. Non-limiting examples of catalysts that promote oxidative coupling of methane to produce ethylene are $Li_2O$, $Na_2O$, $Cs_2O$, MgO, $WO_3$, $Mn_3O_4$, or any combination thereof. A non-limiting example of a mixture of catalysts is a catalyst mixture that includes a supported catalyst containing Ni, Ce and La, and another supported catalyst containing Mn, W, and Na (e.g., Mn—$Na_2WO_4$ on $SiO_2$). In some instances, the second catalyst has a $C_2$+ selectivity that is greater than the first catalyst.

B. Reactants

The reactant mixture in the context of the present invention is a gaseous mixture that includes, but is not limited to, a hydrocarbon or mixtures of hydrocarbons and oxygen. The hydrocarbon or mixtures of hydrocarbons can include natural gas, liquefied petroleum gas containing of $C_2$-$C_5$ hydrocarbons, $C_6$+ heavy hydrocarbons (e.g., $C_6$ to $C_{24}$ hydrocarbons such as diesel fuel, jet fuel, gasoline, tars, kerosene, etc.), oxygenated hydrocarbons, and/or biodiesel, alcohols, or dimethyl ether. In a preferred aspect, the hydrocarbon is a mixture of hydrocarbons that is predominately methane (e.g., natural gas). The oxygen containing gas used in the present invention can be air, oxygen enriched air, oxygen gas, and can be obtained from various sources. The reactant mixture may further contain other gases, provided that these do not negatively affect the reaction. Examples of such other gases include carbon dioxide, nitrogen and hydrogen. The hydrogen may be from various sources, including streams coming from other chemical processes, like ethane cracking, methanol synthesis, or conversion of methane to aromatics. Carbon dioxide may be from natural gas, or a waste or recycle gas stream (e.g. from a plant on the same site, like for example from ammonia synthesis) or after recovering the carbon dioxide from a gas stream.

C. Oxidative Coupling of Methane Process

In one particular aspect of the invention, a method of producing ethylene from a reaction mixture that includes methane ($CH_4$) and an oxygen ($O_2$) containing gas is described. The reaction mixture can be contacted with the metal oxide catalyst of the present invention under sufficient conditions to produce a product stream (e.g., a first product stream) that includes ethylene. The ethylene is obtained from oxidative coupling of $CH_4$. In some instances, continuous flow reactors can be used in the context of the present invention to treat methane with oxygen to produce ethylene. Non-limiting examples of continuous flow reactors include a fixed-bed reactor, a fluidized reactor, a stacked bed reactor, an ebullating bed reactor, or a moving bed reactor. The reactors include conventional components for controlling chemical reactions such as, for example, heating elements, thermocouples, manual and/or automated controllers, valves, and the like. The reactors can be jacketed or unjacketed. Jacketed reactors can be capable of circulating a heat exchange fluid for addition or removal of heat as necessary during the chemical reaction. In some aspects of the present invention, the reactant mixture can have a molar ratio of $CH_4$ to $O_2$ ranges from 0.3 to 20, 0.5 to 15, 1 to 10, or 5 to 7.5 or any range there between. The molar ratio of $CH_4$ to $O_2$ can be 0.3, 0.5, 1, 1.5, 2, 2.5, 3, 3.5, 4, 4.5, 5, 5.5, 6, 6.5, 7, 7.5, 8, 8.5, 9, 9.5, 10, 15, or 20 or any value there between. Process conditions to effect production of ethylene from methane through oxidative coupling can include an average temperature of less than 1000° C., less than 700° C., 275° C. to 700° C., 400 to 550° C. or from 425 to 525° C. and a pressure of about 1 bara, and/or a gas hourly space velocity (GHSV) from 500 to 50,000 h$^{-1}$ or more. In a preferred embodiment, the reactant mixture is heated to an average temperature of less than 700° C., preferably 275° C. to 700° C., more preferably 300° C. to 550° C. or most preferably from 300° C. to 450° C. In some embodiments, the metal oxide catalyst and the reactant mixture are heated to the same temperature and the temperature downstream of the metal oxide catalyst is maintained at a different temperature. Severity of the process conditions may be manipulated by changing, the hydrocarbon source, oxygen source, carbon dioxide source, pressure, flow rates, the temperature of the process, the catalyst type, and/or catalyst to feed ratio. A process in accordance with the present invention is carried out at pressures more than atmospheric pressure.

In some embodiments, the catalyst is used in combination with the second catalyst described above that is capable of catalyzing an oxidative coupling of methane reaction to produce a second product stream that includes $C_2$+ hydrocarbons. Such a combination produces a greater amount of $C_2$+ hydrocarbons in the second product stream than those produced in the first product stream. The second catalyst can be positioned downstream from the first catalyst. When the metal oxide catalyst of the present invention (first catalyst) is used in combination with the second catalyst and positioned upstream from the second catalyst, the reactant feed can be at a lower average temperature relative to average temperatures conventionally used for oxidative coupling of methane. In some instances, the average temperature of the reactant feed just prior to or during contact with the first catalyst is 275° C. to less than 700° C., 300 to 550° C., or preferably 300° C. to 450° C. at a GHSV of 500 to 10,000 h$^{-1}$. In some embodiments, the feed can be heated to the same temperature as the first reaction zone. Heat generated during the oxidative coupling of methane between the reactant feed and the first catalyst can be used to heat the first product stream. The use of a catalyst that can ignite the oxidative coupling of methane at relatively low temperature in combination with another catalyst allows for higher $C_2$+ yield while extending catalyst life by inhibiting sintering of catalytic metals and/or agglomeration of particles in the catalyst.

Referring to FIG. 1, a schematic of system 100 for the production of ethylene is depicted. System 100 may include a continuous flow reactor 102 and a catalytic material 104. In a preferred embodiment, catalytic material 104 is the La—Ce oxide catalytic material of the present invention. A reactant stream that includes methane can enter the continuous flow reactor 102 via the feed inlet 106. An oxygen containing gas (oxidant) is provided in via oxidant source inlet 108. In some aspects of the invention, methane and the oxygen containing gas are fed to the reactor via one inlet. The reactants can be provided to the continuous flow reactor 102 such that the reactants mix in the reactor to form a reactant mixture prior to contacting the catalytic material 104. The average temperature of reactant mixture prior to contacting the catalytic material is less than 1000° C., or 275° C., 300° C. to 700° C., 450° C. to 550° C., or 400° C. to 525° C. or any range there between. In some embodiments, the catalytic material is heated to an average temperature of less than 1000° C., or 275° C., 300° C. to 700° C., 450° C. to 550° C., or 400° C. to 525° C. or any range there between. The average temperature of the reactant mixture, the catalytic material, or both can be 300° C., 325° C., 350° C., 375° C., 400° C., 425° C., 450° C., 475° C., 500° C., 525° C., 550° C., 600° C., 625° C., 650° C., or 700° C. In some instances, the catalytic material 104 may be layered in the continuous flow reactor 102. Contact of the reactant mixture with the first catalytic material 104 produces a product stream (for example, ethylene and generates heat (i.e., an exotherm or rise in temperature is observed). After ignition, the reaction conditions are maintained downstream of the first catalyst at temperatures sufficient to promote continuation of the process. Wishing not to be bound by theory, it is believed that the product stream from contact of the feed stream with the catalytic material in the presence of oxygen at lower average temperatures does not generate excessive heat, thus only a small amount or substantially no carbon dioxide or carbon monoxide is formed resulting in a relatively high $C_2$+ selectivity. The product stream can exit continuous flow reactor 102 via product outlet 110.

Figure 2A:
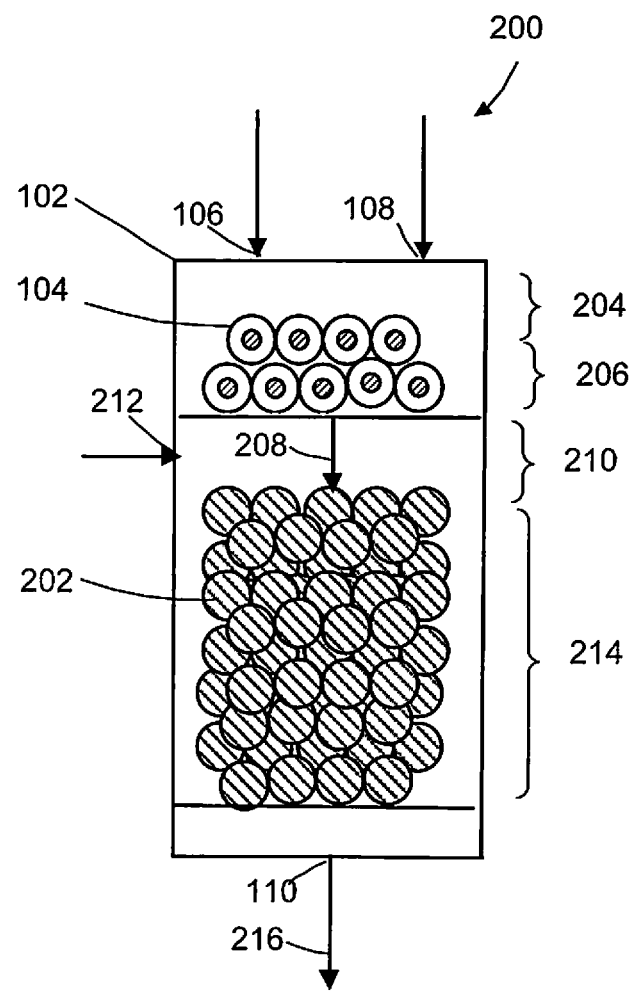
FIGS. 2A and 2B are schematics of embodiments of a system to produce ethylene using the catalytic material of the present invention and an additional catalyst.
Figure 2B:
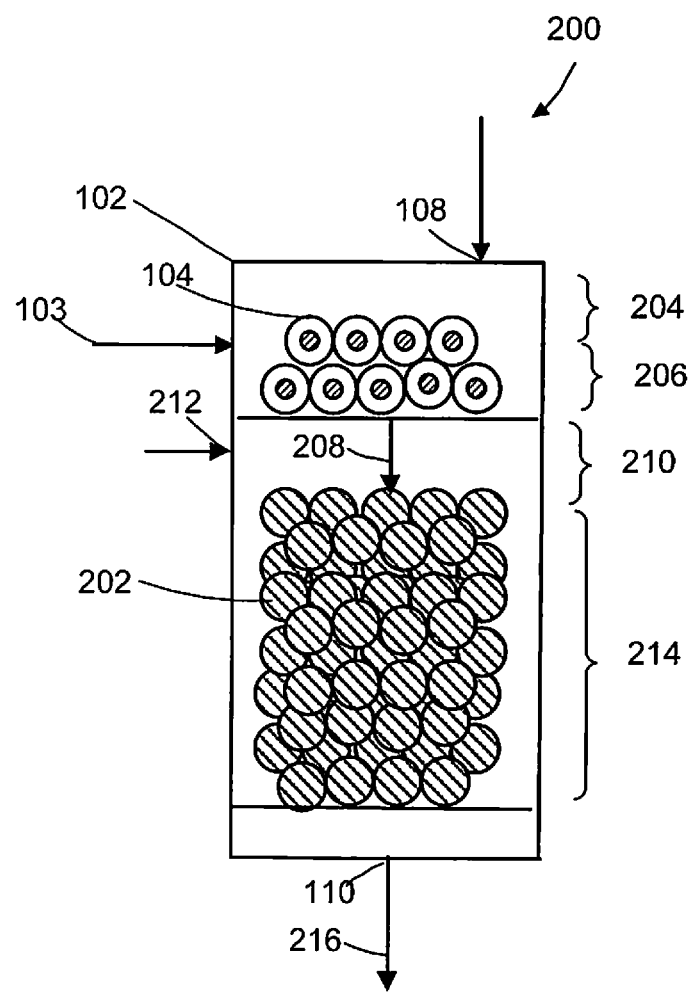

Referring to FIGS. 2A and 2B, a schematic of system 200 having the catalyst of the present invention and a second catalyst is described for the production of ethylene. System 200 may include a continuous flow reactor 102, a first catalytic material 104, and a second catalytic material 202 positioned downstream of the first catalytic material. The first catalytic material 104 can be the catalytic material of the present invention and second catalytic material 202 can the same or different as catalytic material 104. In a preferred embodiment, second catalytic material 202 is a catalytic material that has a higher $C_2$+ selectivity than the first catalytic material 104. A reactant stream that contains methane enters the continuous flow reactor 102 via the feed inlet 106. An oxygen containing gas is provided in via oxidant source inlet 108. The reactants can be provided to the continuous flow reactor 102 such that the reactants mix in the zone 204 to form a reactant mixture prior to contacting the first catalytic layer 104. In some embodiments, the reactants can be provided to the continuous flow reactor 102 are provided as one stream via one inlet. As shown in FIG. 2B, a mixture of methane (e.g., hydrocarbon gas) and an oxygen containing gas can enter continuous flow reactor via inlet 103 and an additional oxygen containing gas can be added via oxidant inlet 108. The average temperature of the reactant mixture in zone 206 prior to contacting the catalytic material is less 1000° C., or 275° C., 300° C. to 700° C., 450° C. to 550° C., or 400° C. to 525° C. or any range there between. The GHSV can be adjusted to, or be maintained at, 500 hr$^{-1}$ or more. In some embodiments, the reaction zone 206 and/or catalytic material 104 is heated to an average temperature of less than 1000° C., or 275° C., 300° C. to 700° C., 450° C. to 550° C., or 400° C. to 525° C. or any range there between. Contact of the reactant mixture with the first catalytic material 104 in reaction zone 206 produces a first product stream 208 (for example, ethylene and generates heat (i.e., an exotherm or rise in temperature is observed). The first product stream 208 can include unreacted methane, oxygen containing gas, and $C_2$+ hydrocarbons. A portion of the generated heat in reaction zone 206 is transferred to the first product stream 208. In a preferred embodiment, the first product stream 208 is heated only by heated generated from contact of the reactant mixture with the first catalytic material 104. As shown in FIG. 2B, the first catalytic material 104 and second catalytic material 202 are separated with zone 210, however, the two catalytic materials may be positioned such that there is a minimal amount of space between the two catalytic layers. In some embodiments, the amount of oxygen in the oxygen containing gas is monitored, and if more oxygen is necessary, oxygen can be added to zone 210 via oxygen containing gas source inlet 212. In a preferred embodiment, at least 90% or substantially all (e.g., 100%) of the oxygen provided to the reactant mixture is converted, and thus, additional oxygen is provided via oxidant inlet 212 to zone 210. The first product stream 208 can be heated prior to and during contact with the second catalytic material 202. In a preferred embodiment, heat from reaction zone 206 heats the first product stream and/or the oxygen containing gas to a temperature of at least 700° C., or 700° C. to 1000° C., 700° C. to 900° C. The heated product steam with sufficient oxygen either remaining in the stream or from an external source (e.g., from the oxygen containing gas entering via inlet 212 shown in FIG. 2B) can enter reaction zone 214. The reaction zone 214 can be heated to an average temperature of at least 700° C., or 700° C. to 1000° C., 700° C. to 900° C. by the heat generated in zone 206 and/or by the heat generated in zone 214. The GHSV can be adjusted to or maintained at a rate higher than the first reaction zone (e.g., 5,000 hr$^{-1}$ or more, 10,000 hr$^{-1}$ or more, 20,000 hr$^{-1}$ or more, 50,000 hr$^{-1}$ or more, 60 hr$^{-1}$ or more, or 80,000 hr$^{-1}$ or more, preferably higher than 50,000 hr$^{-1}$). Contact of the heated first product stream 208 with the second catalytic material in the presence of oxygen in reaction zone 214 generates a second product stream 216. In some embodiments, contact of the reactant mixture with the first catalyst is controlled such that the methane conversion is greater than zero, but as low as possible. Said another way, the reaction is started using the first catalyst and then maintained using the second catalytic material. Use of an igniting catalyst and a high selectivity catalyst can provide high selectivities to $C_2$+ hydrocarbon with prolonged catalyst life (e.g., sintering and coking of the catalyst are minimized). Second product stream 216 can have more $C_2$+ hydrocarbons than the first product stream 206. The second product stream 216 can exit continuous flow reactor 102 via product outlet 110. While only two layers of catalytic material is described it should be understood that additional catalysts can be positioned downstream of the second catalytic material to achieve the desired C₂+ hydrocarbons. The additional catalysts can be any of the catalysts described throughout the invention.

The resulting C₂+ hydrocarbons and water produced from the systems of the invention (for example, systems 100 and 200) can be collected in a collection device and/or transported via piping to separation unit. In the separation unit, the C₂+ hydrocarbons are separated using known separation techniques, for example, distillation, absorption, membrane technology to produce an ethylene product. In embodiments when carbon dioxide is in the reactant mixture and/or generated in situ, the resulting gases (for example, CO, H₂, and ethylene) produced from the systems of the invention (for example, systems 100 and 200) is separated from the hydrogen, carbon monoxide, and carbon dioxide (if present) using known separation techniques, for example, a hydrogen selective membrane, a carbon monoxide selective membrane, a carbon dioxide selective membrane, or cryogenic distillation to produce one or more products such as ethylene, carbon monoxide, carbon dioxide, hydrogen or mixtures thereof. The separated or mixture of products can be used in additional downstream reaction schemes to create additional products or for energy production. Examples of other products include chemical products such as methanol production, olefin synthesis (e.g., via Fischer-Tropsch reaction), aromatics production, carbonylation of methanol, carbonylation of olefins, the reduction of iron oxide in steel production, etc. The method can further include isolating and/or storing the produced gaseous mixture or the separated products.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Synthesis of Catalysts

All materials for the synthesis of the bulk metal oxide catalysts were obtained from Sigma Aldrich Chemical Company (St. Louis, Mo., USA).

Bulk Metal Oxide Catalyst.

Figure 3:
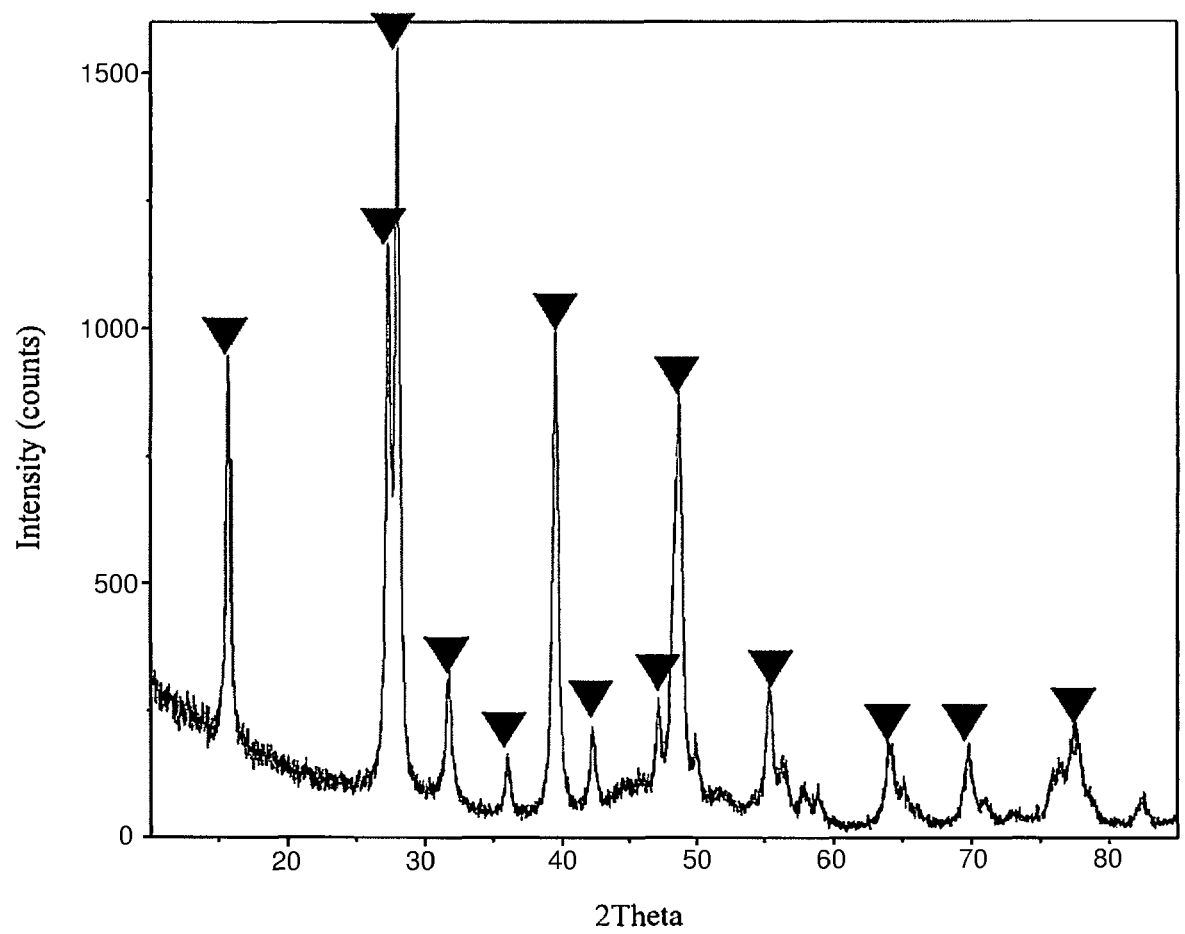
FIG. 3 is an image of an X-Ray Diffraction pattern of catalyst of the present invention having a molar ratio of La:Ce of 15.
Figure 4:
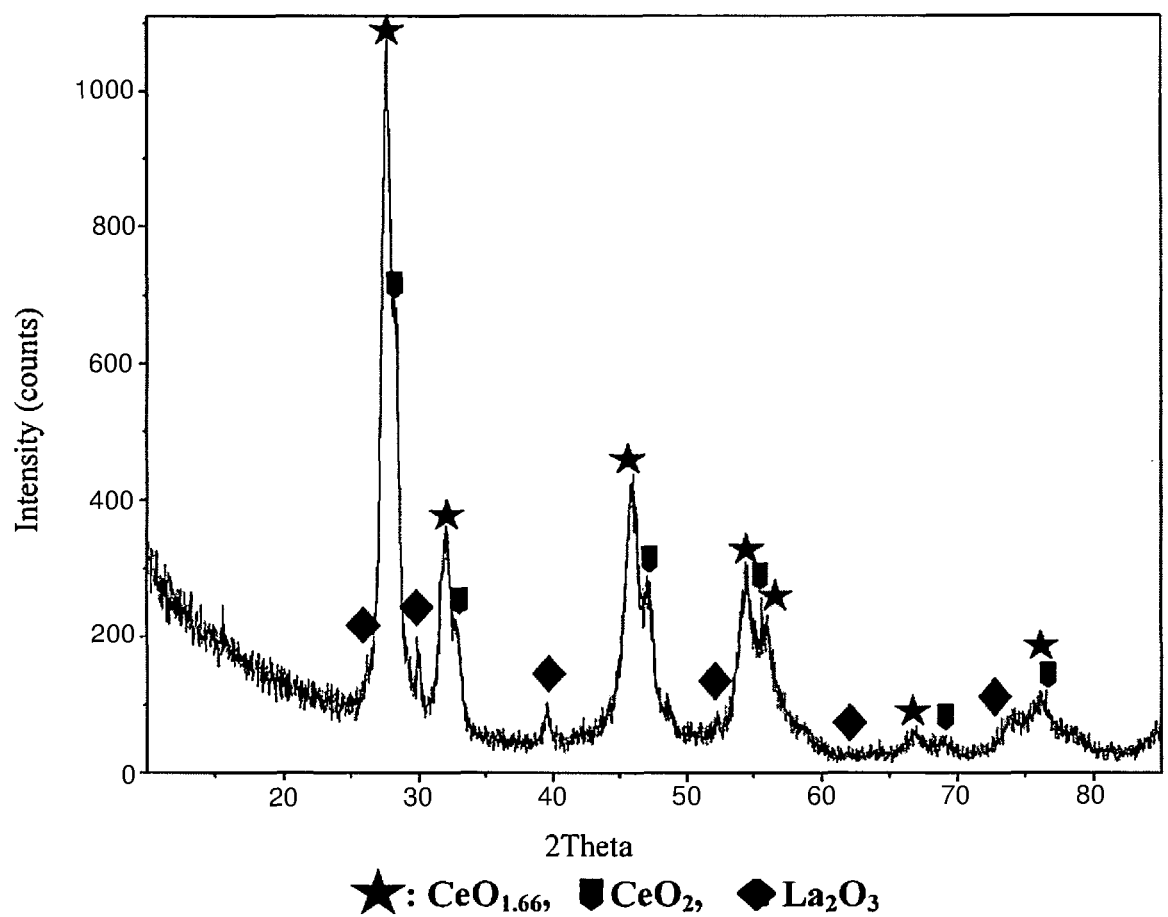
FIG. 4 is an image of X-Ray Diffraction pattern of catalyst having a molar ratio of La:Ce of 1.

Lanthanum nitrate (La(NO₃)₃) and cerium nitrate (Ce(NO₃)₃) in the molar ratios shown below in Table 1 were dissolved in de-ionized water under agitation. Then the mixture was dried at 125° C. overnight. The dried material was then calcined at 625° C. for 5 hours at a ramp rate of 1° C. per minute. FIG. 3 is an X-Ray Diffraction (XRD) patterns of bulk metal oxide catalyst of the present invention (sample 3 in Table 1) showing the La(OH)₃ phase. The upside down triangle indicates the peaks attributable to the La(OH)₃. As shown in FIG. 3, the La(OH)₃ phase is the dominant phase in the catalyst. FIG. 4 is an X-Ray Diffraction (XRD) patterns of Sample 5 which did not include the La(OH)₃ phase.

TABLE 1

| Sample No. | La/Ce (Molar Ratio) | Presence of La(OH)₃ Crystal Phase |
|---|---|---|
| 1 | 10 | yes |
| 2 | 30 | yes |
| 3 | 15 | yes |
| 4 | 7 | yes |
| 5 | 1 | no |

Example 2

Oxidative Coupling of Methane

A fixed bed catalyst reactor was filled with a catalytic material of Example 1 (10 mg). The reactor was heated to the required temperature, and a mixture of methane (CH₄) and oxygen (O₂) at a fixed CH₄:O₂ ratio of 7.4 was fed to the reactor at a flow rate of 80 sccm. The ignition temperature, methane conversion, oxygen conversion and selectivity to C₂⁺ products under 500° C. for each sample are listed in Table 2. Methane conversion was calculated on the basis of difference of inlet and outlet concentrations of methane. Selectivity was calculated on the basis of concentrations of C₂+ products in comparison all the converted amount of methane. From analysis of the data, it was concluded that the catalysts containing La(OH)₃ crystal phase showed higher C₂+ selectivity than the catalyst without the La(OH)₃ crystal phase.

TABLE 2

| Sample No. | Ignition Temperature, ° C. | O₂ Conversion, % | CH₄ Conversion, % | C₂+ Selectivity, % |
|---|---|---|---|---|
| 1 | 500 | 98.8 | 15.5 | 67.0 |
| 2 | 450 | 78.2 | 14.2 | 63.1 |
| 3 | 500 | 92.1 | 15.6 | 62.9 |
| 4 | 450 | 99.5 | 16.4 | 68.5 |
| 5 | 450 | 93.9 | 10.6 | 59.5 |

Figure 5:
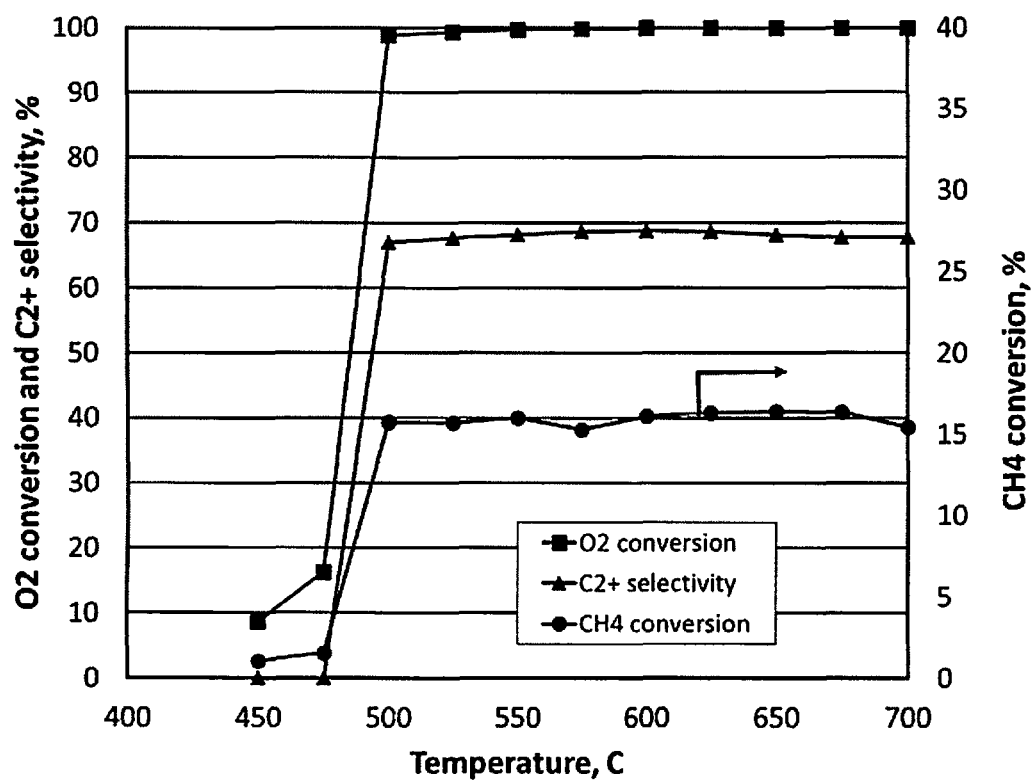
FIG. 5 are graphs of temperature in Celsius versus $O_2$ conversion in percent, $CH_4$ conversion in percent and $C_2+$ selectivity in percent for Sample 1 (La:Ce ratio of 10:1) in an oxidative coupling of methane reaction.
Figure 6:
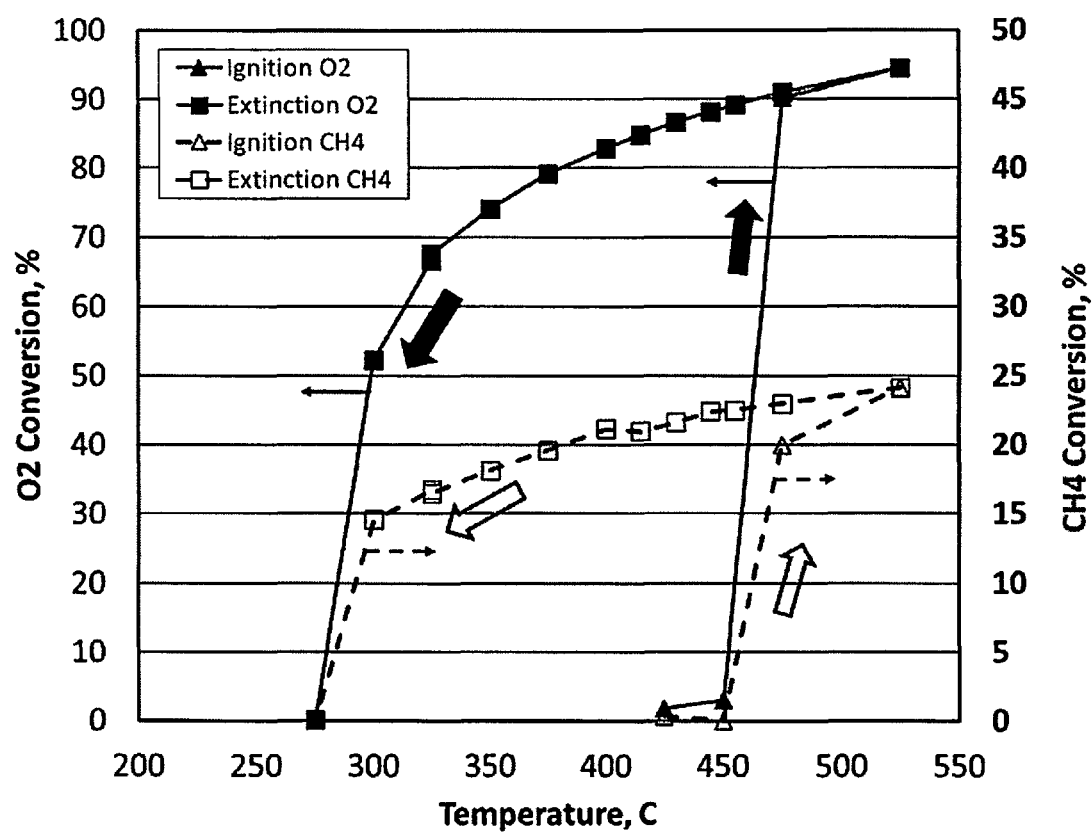
FIG. 6 are graphs of temperature in Celsius versus $O_2$ conversion in percent, $CH_4$ conversion in percent for Sample 3 (La:Ce ratio of 15:1) in an oxidative coupling of methane reaction at a methane to oxygen ratio of 4.

FIG. 5 are graphs of O₂ conversion in percent, CH₄ conversion in percent and C₂+ selectivity in percent versus temperature in Celsius for Sample 1 (La:Ce ratio of 10:1) in an oxidative coupling of methane reaction. From analysis of the data, it was concluded that the reaction ignited at 500° C. FIG. 6 are graphs of O₂ conversion in percent, CH₄ conversion in percent versus temperature in Celsius for Sample 3 (La:Ce ratio of 15:1) in an oxidative coupling of methane reaction under a methane to oxygen ratio of 4.0. Under these operation conditions, the reaction ignited at about 475° C. It was observed that the reaction extinction temperature under these conditions was 275° C. Thus, a high level of CH₄ conversion can be obtained at operation temperature above 275° C.

Example 3

Oxidative Coupling of Methane with a Second Catalyst

A fixed bed catalyst reactor was filled with a supported catalyst (100 mg, MnNa₂WO₄/SiO₂). The reactor was heated to the required temperature and methane and oxygen was fed to the reactor at a flow rate of 33.3 sccm. The CH₄:O₂ ratio, methane conversion, oxygen conversion and with selectivity to C₂+ products for each sample is listed in Table 3. Methane conversion was calculated on the basis of difference of inlet and outlet concentrations of methane. Selectivity was calculated on the basis of concentrations of $C_2+$ products in comparison all the converted amount of methane.

TABLE 3

| Sample No. | $CH_4$:$O_2$ ratio | Reaction Temperature, °C. | $O_2$ Conversion, % | $CH_4$ Conversion, % | $C_2+$ Selectivity, % |
|---|---|---|---|---|---|
| 6 | 4.0 | 750 | 100 | 30.4 | 73.3 |
| 7 | 7.4 | 800 | 100 | 18.8 | 79.8 |

From analysis of the data in Table 3, the selectivities with the second catalyst in the presence of oxygen were determined to be higher than those obtained from the catalysts used in Example 2.

The invention claimed is:

1. A method of producing $C_2+$ hydrocarbons from an oxidative coupling of methane reaction, the method comprising:
   (a) providing a reactant feed that comprises methane and an oxygen containing gas to a first reaction zone having a first oxidative coupling of methane catalyst to cause the oxidative coupling of methane reaction in the first reaction zone, wherein the temperature of the reactant feed entering the first reaction zone is 275° C. to less than 550° C., and wherein $C_{2+}$ hydrocarbon selectivity in the first reaction zone is at least 60%;
   (b) performing oxidative coupling of the methane in the reactant feed over the first oxidative coupling of methane catalyst at a temperature of less than 700° C. to produce a first product stream comprising $C_2+$ hydrocarbons, unreacted methane and heat, wherein the $C_{2+}$ hydrocarbon selectivity in the first reaction zone is at least 60%; and
   (c) performing oxidative coupling of the unreacted methane in the first product stream over a second oxidative coupling of methane catalyst at a temperature of at least 700° C. to produce a second product stream comprising $C_2+$ hydrocarbons, wherein the amount of $C_{2+}$ hydrocarbons in the second product stream is greater than the amount of $C_{2+}$ hydrocarbons in the first product stream, wherein heat produced in step (b) is at least partially used to heat the first product stream or the second reaction zone prior to or during contact with the second catalyst, and
   wherein the first catalyst or second catalyst are each individually a bulk metal catalyst.

2. The method of claim 1, wherein the temperature of the reactant feed just prior to or during contact with the first catalyst is 300° C.

3. The method of claim 1, wherein the temperature of the first product stream just prior to or during contact with the second catalyst is 1000° C.

4. The method of claim 1, wherein the first catalyst, the second catalyst or both comprises lanthanum or a compound thereof, cerium or a compound thereof, silicon or a compound thereof, and any combination thereof.

5. The method of claim 1, wherein the first product stream, prior to being contacted with the second catalyst, is contacted with an oxygen gas feed.

6. The method of claim 1, wherein the temperature of the reactant feed in step (a) is 275° C., and the oxidative coupling of methane reaction in step (b) occurs at a temperature of from 300° C.

7. The method of claim 6, wherein $C_2+$ hydrocarbon selectivity in the first reaction zone is at least 70%.

8. The method of claim 1, wherein overall $C_{2+}$ hydrocarbon selectivity of the second catalyst is at least 70%.

9. The method of claim 8, wherein the overall $O_2$ conversion is at least 95%.

10. The method of claim 1, wherein the temperature of the first product stream just prior to or during contact with the second catalyst is 700° C. to 1000° C.

11. A method of producing $C_2+$ hydrocarbons from an oxidative coupling of methane reaction, the method comprising:
   (a) providing a reactant feed that comprises methane and an oxygen containing gas to a first reaction zone having a first oxidative coupling of methane catalyst to cause the oxidative coupling of methane reaction in the first reaction zone, wherein the temperature of the reactant feed entering the first reaction zone is 275° C. to less than 550° C., and wherein $C_{2+}$ hydrocarbon selectivity in the first reaction zone is at least 60%;
   (b) performing oxidative coupling of the methane in the reactant feed over the first oxidative coupling of methane catalyst at a temperature of less than 700° C. to produce a first product stream comprising $C_2+$ hydrocarbons, unreacted methane and heat, wherein the $C_{2+}$ hydrocarbon selectivity in the first reaction zone is at least 60%; and
   (c) performing oxidative coupling of the unreacted methane in the first product stream over a second oxidative coupling of methane catalyst at a temperature of at least 700° C. to produce a second product stream comprising $C_2+$ hydrocarbons, wherein the amount of $C_{2+}$ hydrocarbons in the second product stream is greater than the amount of $C_{2+}$ hydrocarbons in the first product stream, wherein heat produced in step (b) is at least partially used to heat the first product stream or the second reaction zone prior to or during contact with the second catalyst;
   wherein the first catalyst or second catalyst are each individually a bulk metal catalyst or a supported catalyst, wherein the supported catalyst comprises the bulk metal catalyst on a support;
   wherein the first catalyst, the second catalyst or both comprise manganese or a compound thereof, tungsten or a compound thereof, lanthanum or a compound thereof, sodium or a compound thereof, cerium or a compound thereof, silicon or a compound thereof, and any combination thereof; and
   wherein the first catalyst comprises a lanthanum (La) cerium (Ce) metal oxide having a lanthanum hydroxide $(La(OH)_3)$ crystalline phase.

12. A method of producing $C_2+$ hydrocarbons from an oxidative coupling of methane reaction, the method comprising:
   (a) providing a reactant feed that comprises methane and an oxygen containing gas to a first reaction zone having a first oxidative coupling of methane catalyst to cause the oxidative coupling of methane reaction in the first reaction zone, wherein the temperature of the reactant feed entering the first reaction zone is 275° C. to less than 550° C., and wherein C2+ hydrocarbon selectivity in the first reaction zone is at least 60%;
   (b) performing oxidative coupling of the methane in the reactant feed over the first oxidative coupling of methane catalyst at a temperature of less than 700° C. to produce a first product stream comprising $C_2+$ hydrocarbons, unreacted methane and heat, wherein the $C_{2+}$ hydrocarbon selectivity in the first reaction zone is at least 60%; and (c) performing oxidative coupling of the unreacted methane in the first product stream over a second oxidative coupling of methane catalyst at a temperature of at least 700° C. to produce a second product stream comprising $C_2+$ hydrocarbons, wherein the amount of $C_{2+}$ hydrocarbons in the second product stream is greater than the amount of $C_{2+}$ hydrocarbons in the first product stream, wherein heat produced in step (b) is at least partially used to heat the first product stream or the second reaction zone prior to or during contact with the second catalyst, wherein the first catalyst or second catalyst are each a bulk metal catalyst or a supported catalyst, wherein the supported catalyst comprises the bulk metal catalyst on a support; wherein the first catalyst, the second catalyst or both comprises manganese or a compound thereof, tungsten or a compound thereof, lanthanum or a compound thereof, sodium or a compound thereof, cerium or a compound thereof, silicon or a compound thereof, and any combination thereof; and wherein the second catalyst is a supported catalyst comprising a support, and wherein the support is silicon dioxide, lanthanum oxide, or aluminum oxide, or a combination thereof; and, wherein the second catalyst comprises Mn—$Na_2WO_4$/$SiO_2$ and the first catalyst comprises a lanthanum (La) cerium (Ce) metal oxide having a lanthanum hydroxide ($La(OH)_3$) crystalline phase.

13. A system for producing $C_2+$ hydrocarbons, the system comprising:

(a) an inlet for a reactant feed comprising methane and an oxygen containing gas, wherein the temperature of the reactant feed entering the inlet is 275° C. to less than 700° C.;

(b) a first reaction zone that is configured to be in fluid communication with the inlet, wherein the first reaction zone comprises a first bulk catalyst capable of catalyzing an oxidative coupling of methane reaction and producing a first product stream;

(c) a second reaction zone that is configured to be in fluid communication with the first reaction zone and receive the first product stream from the first reaction zone, wherein the second reaction zone comprises a second catalyst capable of catalyzing an oxidative coupling of methane reaction; and (d) an outlet configured to be in fluid communication with the second reaction zone and configured to remove a second product stream comprising $C_2+$ hydrocarbons from the reaction zone, wherein the amount of $C_2+$ hydrocarbons in the second product stream is greater than the amount of $C_2+$ hydrocarbons in the first product stream, and wherein the second catalyst is a supported catalyst comprising a support, and wherein the support is silicon dioxide or aluminum oxide, or a combination thereof.

14. The system of claim 13, wherein the temperature of the second reaction zone is greater than the temperature of the first reaction zone.

15. The system of claim 14, wherein at least a portion of the heat from the first reaction zone is used to heat the second reaction zone or is used to heat the first product stream or is used to heat both.

16. The system of claim 13, wherein the first catalyst comprises a lanthanum (La) cerium (Ce) metal oxide having a lanthanum hydroxide ($La(OH)_3$) crystalline phase.

17. The system of claim 13, wherein the second catalyst is a supported catalyst comprising a support, and wherein the support is silicon dioxide.

18. The system of claim 17, wherein the second catalyst includes lanthanum or a compound thereof, cerium or a compound thereof, silicon or a compound thereof, and any combination thereof.

* * * * *

UNITED STATES PATENT AND TRADEMARK OFFICE
CERTIFICATE OF CORRECTION

PATENT NO. : 10,696,607 B2
APPLICATION NO. : 15/579385
DATED : June 30, 2020
INVENTOR(S) : Liang et al.

Page 1 of 1

It is certified that error appears in the above-identified patent and that said Letters Patent is hereby corrected as shown below:

In the Claims

In Claim 6, on Column 17, Line 67, remove "from".

Signed and Sealed this
Eleventh Day of August, 2020

Andrei Iancu
*Director of the United States Patent and Trademark Office*